(12) United States Patent
Dordick et al.

(10) Patent No.: US 9,360,475 B2
(45) Date of Patent: Jun. 7, 2016

(54) ENHANCED STABILITY OF PROTEINS IMMOBILIZED ON NANOPARTICLES

(75) Inventors: Jonathan S. Dordick, Schenectady, NY (US); Ravindra S. Kane, Niskayuna, NY (US); Prashanth Asuri, Troy, NY (US); Sandeep S. Karajanagi, Troy, NY (US); Alexey A. Vertegel, Easley, SC (US); Richard W. Siegel, Menands, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 802 days.

(21) Appl. No.: 13/456,571

(22) Filed: Apr. 26, 2012

(65) Prior Publication Data

US 2012/0301870 A1     Nov. 29, 2012

Related U.S. Application Data

(63) Continuation of application No. 11/663,040, filed as application No. PCT/US2005/031652 on Sep. 7, 2005, now abandoned.

(60) Provisional application No. 60/607,816, filed on Sep. 8, 2004.

(51) Int. Cl.
  *C07K 14/00*  (2006.01)
  *G01N 33/543*  (2006.01)
  *B82Y 15/00*  (2011.01)
  *C12Q 1/00*  (2006.01)
  *G01N 33/58*  (2006.01)

(52) U.S. Cl.
  CPC .......... *G01N 33/54346* (2013.01); *B82Y 15/00* (2013.01); *C12Q 1/001* (2013.01); *G01N 33/587* (2013.01); *G01N 33/588* (2013.01)

(58) Field of Classification Search
  None
  See application file for complete search history.

(56) References Cited

PUBLICATIONS

Vertegel et al., "Silica Nanoparticle Size Influences the Structure and Enzymatic Activity of Adsorbed Lysozme", Langmuir 2004, 20, 6800-6807.*
Keating et al., "Protein:Colloid Conjugates for Surface Enhanced Raman Scattering: Stability and Control of Protein Orientation", J. Phys. Chem. B. 1998, 102, 9404-9413.*
Shang, W., et al., "Cytochrome c on Silica Nanoparticles: Influence of Nanoparticle Size on Protein Structure, Stability, and Activity," Small, 5: 470-476 (2009).

* cited by examiner

*Primary Examiner* — Anand Desai
(74) *Attorney, Agent, or Firm* — Elmore Patent Law Group, P.C.; Mahreen Chaudhry Hoda; Carolyn S. Elmore, Esq.

(57) ABSTRACT

This invention is directed to the application of a previously unknown property of nanomaterials—its ability to enhance protein activity and stability at high temperatures, in organic solvents, and in polymer composites. Nanomaterials such as single-walled carbon nanotubes (SWNTs) can significantly enhance enzyme function and stability in strongly denaturing environments. Experimental results and theoretical analysis reveal that the enhancement in stability is a result of the curvature of these nanoscale materials, which suppresses unfavorable protein-protein interactions.

19 Claims, 4 Drawing Sheets

ENHANCED STABILITY OF PROTEINS IMMOBILIZED ON NANOPARTICLES

RELATED APPLICATIONS

This application is a continuation of U.S. application Ser. No. 11/663,040, filed Jan. 2, 2009, which is a US National stage entry of International Application No. PCT/US2005/031652, which designated the United States and was filed on Sep. 7, 2005, published in English, which claims the benefit of U.S. Provisional Application No. 60/607,816, filed on Sep. 8, 2004. The entire teachings of the above applications are incorporated herein by reference.

GOVERNMENT SUPPORT

The invention was supported, in whole or in part, by a grant from the National Science Foundation (DMR-0117792). The Government has certain rights in the invention.

BACKGROUND OF THE INVENTION

Interfacing nanomaterials, in particular carbon nanotubes, with biomolecules are important for applications ranging from biosensors, biorecognition probes, and molecular electronics to drug delivery. A major obstacle in the pursuit of applications of these conjugates stems from the poor stability of biomolecules in harsh environments.

SUMMARY OF THE INVENTION

This invention is directed to protein compositions that comprise biologically active proteins that are less susceptible to degradation than normal. For example, this invention is directed to compositions that enzymatically act on substrates where the enzymes of the compositions are less susceptible to degradation than normal. The proteins and enzymes of these compositions can retain biological or enzymatic activity even when the compositions and substrates are in normally harsh or hostile environments, such as abnormal pHs, temperatures, high salinities, or media, including non-aqueous media such as organic solvents, ionic liquids, gaseous media, and supercritical fluids.

The compositions of this invention are proteins, e.g. enzymes, bound to the external surfaces of nanoparticles. These nanoparticles have external surfaces whose radius of curvature is commensurate with the dimensions of each of the proteins or enzymes, that are bound to the nanoparticles. When this size relationship is met, the stability of the bound proteins or enzymes is greater than the stability of these proteins when they are bound to particles or surfaces whose radius of curvature is greater than the dimensions of each of the bound proteins, e.g., the proteins bound to flat surfaces. This stability difference exists even when the material which forms the nanoparticles and the more flat substrata are the same. The enhanced stability of the compositions of this invention is maintained when the compositions are attached to a macroscopic surface or are embraced within the polymer.

This invention is also directed to methods of detecting analytes, even when the analytes are in a solution that provides a harsh or hostile environment for enzymes. At least a portion of these analytes is normally a substrate for the enzymes. The analyte detection methods of this invention utilize the compositions of this invention that contain the appropriate enzymes.

This invention is also directed to methods for preventing fouling of surfaces by fouling agents. These fouling agents are also substrates for enzymes and are often found in media that constitute a harsh or hostile environment for the enzymes. In this invention, the compositions of this invention are used to rid the media of these fouling agents by enzymatically degrading the agents, thereby keeping surfaces, which are often fouled by the agents, free of these fouling agents.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

A core aspect of this invention is the formation of nanoparticles with proteins or enzymes attached to their external surfaces. These nanoparticles can be formed by a variety of techniques and from a variety of materials known in the art of nanoparticle fabrication. The nanoparticles that are suitable in this invention generally include nanomaterials, e.g., nanotubes, nanosheets, nanoporous materials, such as single-walled carbon nanotubes, multi-walled carbon nanotubes, gold nanoparticles or other metallic, semi-conducting, or metal oxide nanoparticles, quantum dots, functionalizes silica. Single-walled carbon nanotubes are preferred.

Proteins which can be used in this invention include proteins which possess a biological activity. A biological activity includes commercially relevant activities as a diagnostic, therapeutic, enzymatic or other protein activity. Examples of proteins include immunoglobulin-like proteins; antibodies; cytokines (e.g., lymphokines, monokines and chemokines); interleukins; interferons; erythropoietin; hormones (e.g., growth hormone and adrenocorticotropic hormone); growth factors; nucleases; tumor necrosis factor; colony-stimulating factors; insulin; antigens (e.g., bacterial and viral antigens); DNA-binding proteins and tumor suppressor proteins.

The enzymes of this invention can be of any type. The enzyme species is not a critical aspect of the invention. Proteases, peroxidases, lipases, carbohydrate cleavage enzymes, carbohydrases, esterases, carboxylases, peroxidases, nucleases, lyases, ligases, isomerases, transferases, etc. can be used. The only requirements for each enzyme to be employed in the invention are that it enzymatically acts on the substrate of interest that is present in a solution to which the compositions of this invention are to be exposed, and that it be bindable to the nanoparticles of the compositions.

By way of example, transferases are enzymes transferring a group, for example, the methyl group or a glycosyl group, from one compound (generally regarded as donor) to another compound (generally regarded as acceptor). For example, glycosyltransferases (EC 2.4) transfer glycosyl residues from a donor to an acceptor molecule. Some of the glycosyltransferases also catalyze hydrolysis, which can be regarded as transfer of a glycosyl group from the donor to water. The subclass is further subdivided into hexosyltransferases (EC 2.4.1), pentosyltransferases (EC 2.4.2) and those transferring other glycosyl groups (EC 2.4.99, Nomenclature Committee of the International Union of Biochemistry and Molecular Biology (NC-IUBMB)).

Oxidoreductases catalyze oxido-reductions. The substrate that is oxidized is regarded as hydrogen or electron donor. Oxidoreductases are classified as dehydrogenases, oxidases, mono- and dioxygenases. Dehydrogenases transfer hydrogen from a hydrogen donor to a hydrogen acceptor molecule. Oxidases react with molecular oxygen as hydrogen acceptor and produce oxidized products as well as either hydrogen peroxide or water. Monooxygenases transfer one oxygen atom from molecular oxygen to the substrate and one is reduced to water. In contrast, dioxygenases catalyze the insert of both oxygen atoms from molecular oxygen into the substrate.

Lyases catalyze elimination reactions and thereby generate double bonds or, in the reverse direction, catalyze the additions at double bonds. Isomerases catalyze intramolecular rearrangements. Ligases catalyze the formation of chemical bonds at the expense of ATP consumption.

Hydrolases are enzymes that catalyze the hydrolysis of chemical bonds like C—O or C—N. The E.C. classification for these enzymes generally classifies them by the nature of the bond hydrolysed and by the nature of the substrate. Hydrolases such as lipases and proteases play an important role in nature as well in technical applications of biocatalysts. Proteases hydrolyse a peptide bond within the context of an oligo- or polypeptide. Depending on the catalytic mechanism proteases are grouped into aspartic, serine, cysteine, metallo- and threonine proteases (Handbook of proteolytic enzymes. (1998) Eds: Barret, A; Rawling, N.; Woessner, J.; Academic Press, London).

Since the enzyme species is not a critical aspect of this invention, the substrate type is also not critical. Any substrate can be the target, provided it is enzymatically recognized by the enzyme species on the surface of the nanoparticles of the compositions of this invention, and that it is present in a solution to which the compositions of this invention are to be exposed.

The enzymes can be attached to the nanoparticles to form the compositions of this invention by any suitable technique known in the art. Any chemical or physical bonding can be used. Hydrophobic bonding, hydrophilic bonding, ionic bonding, covalent and non-covalent bonding are suitable bonding types. Of these, hydrophobic bonding is preferred. A major consideration for the choice of bonding process to be employed is that the specific enzyme species bonded to the nanoparticles retain a substantial fraction (e.g., at least about 30%, such as about 50%, at least about 70% or more) of its native enzymatic activity after the bonding process has been completed.

A feature of the compositions of this invention can be that the surfaces of each of the nanoparticles to which the enzymes are attached have a radius of curvature that is within about 2, or preferably about 1, orders of magnitude of the dimensions of each attached enzyme. Thus, the radius of curvature of the nanoparticles is preferably about 100 nm or less.

The enzymes in the compositions of this invention are active when the compositions are exposed to media, containing the substrates that are atypical for the enzymes in an isolated or unbound state. Although the compositions of this invention exhibit very good enzymatic activity when the compositions are in physiological solutions containing the enzyme substrate, they also exhibit very good activity and stability when the media containing the substrate are considered to present harsh or hostile environments to the enzymes. For example, when the medium is an aqueous medium at an elevated temperature, e.g., greater than 90° C., the enzymatic activity and stability of the compositions of this invention is maintained. If the medium is a hydrocarbon solvent, e.g., an alcohol, the enzymatic stability of the compositions of this invention is greater than on more conventional (e.g., flat) surfaces.

The compositions of this invention have the advantage of retaining activity when placed in liquid environments that are typically noxious to the enzymes when these enzymes are not bound to the nanoparticles that are disclosed in this invention. For example, the compositions of this invention will be used in non-aqueous media, e.g., organic solvents, ionic liquids, gaseous media and supercritical fluids, or in media at abnormal temperatures (e.g., other than 20° C. to 40° C.), or media where the pH is non-physiologically acidic or basic or in media possessing abnormal ionic strengths or salt levels (e.g., media with high salinity, such as sea water or a salt level of at least about 0.3 M NaCl). Of course, it is recognized that proteins that tolerate such conditions are known (thermophilic enzymes, enzymes which tolerate high levels of saline, etc). Thus, one can characterize harshness of an environment as a relative factor as compared to the normal reaction conditions of the enzyme. Thus, an abnormal temperature for a thermophilic enzyme could be above the temperature at which the thermophilic enzyme is active. Likewise, an abnormal salinity for a salt-tolerant enzyme can be above the salinity levels at which the salt-tolerant enzyme is active.

The compositions of this invention will also be used as antifouling agents in paints, marine paints, coatings, lubricants, ointments, etc. These compositions are also intended for use as antimicrobial agents in environments where the antimicrobial activity of the bound enzymes is desired for microbial lysis or inactivation.

Detection of analytes can be achieved by any number of procedures known in the detection art. Formation of fluorescent species when enzymatic action occurs, formation of absorption species when enzymatic action occurs, liberation of fluorescent or absorption tags when enzymatic action occurs, formation of chemically reactive species by enzymatic action that react with suitable target structures which thereby become detectable, formation of an electrically charged species by enzymatic action which can be electrically detected are examples of detection procedures for analytes when the analytes are the targets of the bound enzymes in the compositions of this invention. Often, the analytes are labels that have been attached to chemical moieties whose detection is sought. In these instances, the analytes are the substrates for the bound enzymes in the compositions of this invention.

The compositions of this invention can be attached to macroscopic surfaces or spread on or embedded within a polymeric material. The compositions of this invention can thereby be made functional parts of useful devices. The compositions of this invention can be added as coatings to medical instruments, biosensors, biochips, biorecognition probes, biocatalytic films, biofuel cells, drug delivery systems, self-cleaning materials, resins, beads, and the like. These compositions can be integral parts of permeable or nonpermeable membranes, sieves, tubing and the like. When incorporated in such devices, the compositions of this invention can be used to detect analytes that are substrates of the enzymes bound to the nanoparticles, to monitor the presence of substances in liquid media that are substrates of these enzymes, to act as antimicrobial agents when the enzyme substrates are integral constituents of viral particles, microbial membranes or cell walls, or to prevent surface fouling by degrading substances that form deleterious films on working surfaces of machines or instruments. There are many utilities available to the skilled artisan for which the compositions of this invention are applicable. Enzymatic activity from solid materials in a liquid environment is assumed to be one of the purposes for the compositions of this invention. Improved enzyme stability when the liquid environment is normally hostile or harsh to the enzymes, when they are dissolved in the liquid, is of particular usefulness with this invention.

The emergence of techniques to generate nanomaterials with precise dimensions, geometries, and surface properties has resulted in an increasingly large number of applications ranging from electronics and high-strength, lightweight materials to sensing elements. To date, proteins, and other biomolecules have been used to functionalize nanomaterials and influence their properties. However, up to now, very little is known about the ability of these nanoscale materials to enhance protein structure and function. Such information, however, is of fundamental importance and is also critical for enhancing protein function and stability on nanoparticles and therefore for designing optimal protein-nanoparticle conjugates for use in functional materials and surface coatings.

Materials and Methods

Enzymes and Reagents. Soybean peroxidase, subtilisin Carlsberg, and N-succinyl-L-ala-L-ala-L-pro-L-phe-p-nitroanilide were purchased from Sigma as salt-free, dry powders and used without further purification. Raw single-walled nanotubes, SWNTs, were purchased from Carbon Nanotechnologies, Inc., highly oriented pyrolytic graphite, HOPG SPI-2, was obtained from Structure Probe, Inc, and graphite was purchased from Aldrich. All the supports were used without further purification. All other chemicals were purchased from Sigma and used as received.

Determination of Enzyme Activity. The initial rates of the phenolic oxidations catalyzed by SBP in presence of $H_2O_2$ were monitored by spectrophotometry. SC cleaves the peptide bond in N-succinyl-L-ala-L-ala-L-pro-L-phe-p-nitroanilide to release a chromophore, p-nitroaniline, and the initial rates were obtained by measuring the increase in the absorbance at 405 nm.

Enzyme Immobilization on SWNTs. The enzymes, Soybean peroxide (SBP) and subtilisin Carlsberg (SC) were adsorbed on SWNTs using hydrophobic interactions. SWNTs were first sonicated in N, N-Dimethyl Formamide (DMF) for 20 minutes to obtain a uniform dispersion of SWNTs in DMF (1 mg/ml). One ml of SWNT dispersion in DMF (i.e. 1 mg of SWNTs) was then dispensed in an Eppendorf micro-centrifuge tube and the organic phase was gradually changed to an aqueous phase by repeated washing with pH 7 buffer (50 mM phosphate). This gradual change from organic phase to an aqueous phase helps in a better dispersibility of SWNTs in buffer. The dispersion of SWNT in pH 7 buffer was then exposed to freshly prepared solutions of enzyme in buffer (pH 7 phosphate, 50 mM). This dispersion was shaken on INNOVA™2000 (New Brunswick Scientific) platform shaker for 2 h at 200 rpm at room temperature. In the case of SC, the shaking was carried out at 4° C. to prevent autolysis of the protease during incubation. After the 2 h incubation, the SWNTs were settled using a micro-centrifuge (Fisher Scientific) and the supenatant was removed. Typically, 6 washes were performed with fresh buffer to remove any unbound/ loosely bound enzyme. All supernatants were analyzed for protein content using the BCA or the µBCA assay (Pierce Biotechnology, Inc.). It was seen that the SWNTs interfere strongly with BCA/µBCA assay. The amount of enzyme loaded on the SWNTs was, therefore, determined by measuring the concentration of enzyme solution before and after exposing it to the dispersion of SWNTs in buffer. The difference in the amount of enzyme gives the amount of enzyme loaded on the SWNTs. A stable value of enzyme loading on SWNTs was obtained by accounting for the loss of enzyme due to leaching during the washes.

Determination of Enzyme Activity. The activity of SBP was measured using the p-Cresol assay. SBP catalyzes the oxidation of p-Cresol by $H_2O_2$ to form oligophenol and polyphenol products that fluoresce. For a typical solution phase assay, the reaction mixture consisted of 0.15 µg/ml solution of SBP (made by serial dilution), 20 mM solution of p-Cresol and 0.125 mM solution of $H_2O_2$ all solutions were made in pH 7.0 buffer (phosphate, 50 mM). The initial rates of reaction were then measured by tracking the increase in fluorescence of the reaction mixture at an excitation wavelength of 325 nm and emission wavelength of 402 nm using a HTS 7000 Plus Bio Assay Reader (Perkin Elmer). For activity measurements in organic solvent phase, the solvents were added during the final wash to make solutions of 0.15 µg/ml solution of SBP in pH 7.0 buffer (phosphate, 50 mM) containing the required amount of solvent in the solution. The p-Cresol and $H_2O_2$ solutions were made in pH 7.0 buffer (phosphate, 50 mM) containing the required concentrations of solvent.

For measuring the activity of SBP immobilized on SWNTs (SWNT-SBP), a well-mixed dispersion of SWNT-SBP (1 mg/ml) was made in buffer and a known amount of SWNT-SBP was dispensed by using serial dilution. For a typical experiment 0.5 µg to 1.5 µg of SWNT-SBP was used based on the loading of the SBP. The enzymatic activity was measured using 20 mM p-Cresol and 0.125 mM $H_2O_2$ in pH 7.0 buffer (phosphate, 50 mM). It was observed that some of the immobilized enzyme leached during the serial dilutions. To account for the effect of the enzyme that would leach during the measurement of the activity of the immobilized enzyme, the SWNT-SBP suspension was washed 6 times more with the same dilutions and buffer used in the final activity measurement. Since the amount of leached enzyme during these washes was too low (<15 ng/ml) to be reliably detected by any of the protein measurement assays, the amount of protein was estimated by measuring the activity of the enzyme in the washes. It was assumed that the activity of the leached enzyme was the same as that of the solution phase enzyme. Using the value of specific activity of the solution phase enzyme and the initial rate of reaction for the enzyme in the wash solution, the amount of enzyme present in the washes was calculated. The final loading of the enzyme on the SWNTs was corrected for this amount of leached enzyme before calculating the specific activity of the immobilized enzyme. After all the washes were done, the SWNT-SBP were dispersed in pH 7.0 buffer (phosphate, 50 mM) and then exposed to the substrate solution so that the final concentrations of the substrates were 20 mM p-Cresol and 0.125 mM $H_2O_2$. The dispersion was shaken at 200 RPM at all times during the reaction using Innova™2000 platform shaker to avoid problems due to diffusion limitations. At fixed time intervals, the SWNTs were settled using a micro-centrifuge and the fluorescence of a 200 μl aliquot of the supernatant was measured using the Bio Assay Reader. The aliquot was then replaced in the reaction mixture. A plot of $H_2O_2$ consumed versus time gives the initial rate of reaction and hence the activity of the SBP immobilized on the SWNTs. For activity measurements in solvent phase, the p-cresol and $H_2O_2$ solutions were made in pH 7.0 buffer (phosphate, 50 mM) containing the required concentrations of solvent. After all the washes, the SWNT-SBP were dispersed in pH 7.0 buffer (phosphate, 50 mM) containing the required amount of solvent and then exposed to the substrate solution. For 100% solvent phase, aqueous SWNT-SBP phase was gradually changed to the organic phase by repeated washing with 100% solvent. This treatment rendered the final concentration of water in the solvent to about 1-2%.

The activity of SC was measured using N-succinyl-L-ala-L-ala-L-pro-L-phe-p-nitoranilide (tetrapeptide) (Sigma-Aldrich) as the substrate. For a typical solution phase assay, 1 μg/ml of freshly prepared SC solution pH 8.0 buffer (phosphate, 50 mM) was used with a 100 μM solution of tetrapeptide in pH 8.0 buffer (phosphate, 50 mM).

Subtilisin Carlsberg, which is a protease, cleaves the peptide bond in the substrate to release the chromophore, p-Nitroaniline, which absorbs at 405 nm. The activity of the enzyme was measured by measuring the increase in the absorbance of the reaction mixture at 405 nm using the Bio Assay Reader. The activity of SC immobilized on SWNTs (SWNT-SC) was measured using the same technique as that used for immobilized SBP (as described above). For SWNT-SC, however, 4 μg to 50 μg of functionalized SWNTs were used for the measurement of activity based on the loading of the SC. After performing 6 washes like those done for SWNT-SBP, the SWNT-SC were dispersed in pH 8 buffer (phosphate, 50 mM) and then exposed to 100 μM tetrapeptide solution (final concentration). The dispersion was kept well mixed by shaking at 200 RPM at all times during the reaction using the platform shaker. At fixed time intervals, the SWNTs were settled using a micro-centrifuge and the absorbance of the supernatant was measured at 405 μm using the Bio Assay Reader. A plot of concentration of p-Nitroaniline versus time gives the initial rate of reaction and hence the activity of the SC immobilized on the SWNTs. The activity measurements in the organic phase were performed as explained above for SBP.

Enzyme Immobilization on Other Supports. The enzymes were also adsorbed on other supports including highly oriented pyrolytic graphite (HOPG), self-assembled monolayers (SAMs) of undecanethiolate on gold (Gold SAM), multi-walled carbon nanotubes (MWNTs), graphite powder (1-2 μm), SWNT films and MWNT films. HOPG SPI-2 samples were obtained from Structure Probe, Inc and fresh surfaces were exposed by peeling off the exposed layers using a scotch tape. Self-assembled monolayers of undecanethiol were assembled from 0.02 mM solutions in absolute ethanol for 12 h. The samples were then removed from the solution and rinsed thoroughly by squirting with ethanol for several seconds. This rinsing was sufficient to remove any unbound thiols from the surface. The synthesis of SWNT and MWNT films was performed by first dispersing SWNTs and MWNTs in pH 7.0 buffer (phosphate, 50 mM) as explained above and filtering the samples through a 0.8 μm ATTP filter. The filter papers with the SWNT and MWNT cakes were dried and were attached to plastic troughs using appropriate clips. SBP and SC were adsorbed in HOPG, Gold SAM, SWNT films, MWNT films by dipping the supports into a solution of the enzymes and shaking the samples on INNOVA™2000 (New Brunswick Scientific) platform shaker for 2 h at 200 rpm at room temperature. In the case of SC, the shaking was carried out at 4° C. to prevent autolysis of the protease during incubation. The samples were then washed 6 times with pH 7.0 buffer (phosphate, 50 mM) to remove any loose/unbound enzyme. The loading on MWNTs was done as described above for SWNTs. After all the washes were done the enzyme bound supports were exposed to the substrate solutions and their activities were measured as outlined above for SWNTs.

The SWNT-enzyme conjugates were prepared in aqueous buffer by adsorbing two model enzymes subtilisin carlsberg (SC) and soybean peroxidase (SBP) onto SWNTs. The enzymes showed strong affinity for SWNTs with saturation levels of 670 and 655 μg/mg SWNT for SC and SBP, respectively. Both SC and SBP retained a substantial fraction of their native enzymatic activity; specific activities of the adsorbed SC and SBP in aqueous buffer were ca. 63% and ca. 38% of the native enzyme activities respectively. FT-IR spectroscopy analysis revealed ca. 11.5% and ca. 13% total change in the secondary structure of SC and SBP respectively due to absorption onto SWNTs. AFM studies also revealed that both SBP and SC retained their tertiary structure on adsorption on SWNTs. This suggests that the present method employed for interfacing SBP and SC with SWNTs results in a minimal loss in the native structure.

Hammett analysis was used as a sensitive probe of transition state structure and enzyme mechanism. The Hammett coefficient (ρ) provides a measure of the sensitivity of SBP's catalytic efficiency to the electronic nature of substituents on phenolic substrates. Hammett analysis revealed p values of 1.7±0.21 and 1.4±0.12 for SWNT-SBP and HOPG-SBP, respectively, in 100% methanol. The comparable values of p suggest that the mechanism of catalysis is similar for SBP adsorbed on the two supports; the significantly greater retention of activity for SBP immobilized on SWNTs than for SBP immobilized on HOPG in 100% methanol is therefore not due to a change in the mechanism of catalysis on the different supports.

It was also found that a variety of proteins differing in both structure and function, including horseradish peroxidase, subtilisin carlsberg, proteinase K, trypsin, and lipase, remain catalytically active upon adsorption onto SWNTs, with specific activities ranging from 40-70% relative to that of the native protein in aqueous buffer.

Having established that a number of enzymes retain activity on SWNTs in aqueous buffer, SWNTs were examined to determine whether the enzymes function in strongly denaturing environments—environments in which native enzymes show poor retention of activity. To that end, SWNT-SBP was added to solutions of buffer containing the denaturant methanol. FIG. 1a shows the retention of activity in solutions containing methanol, i.e. the enzymatic activity in solutions containing methanol normalized to the enzymatic activity in aqueous buffer, for native SBP and SBP adsorbed onto a variety of supports. The specific activity—the activity normalized to the amount of enzyme—for native SBP and the various SBP conjugates in solutions containing methanol was also determined. Native SBP was completely inactive in 100% methanol. However, the SWNT-SBP conjugates retained relatively high catalytic activity, even in neat methanol (FIG. 1a). It is well known that proteins are often stabilized by immobilization onto a support. To assess whether the stabilization of SBP on SWNTs was simply a result of immobilization, the enzyme was absorbed onto graphite flakes. Since a SWNT is similar to a rolled graphene sheet, graphite flakes represent an ideal surface for comparison. As shown in FIG. 1a, SBP was significantly more active on SWNTs than on graphite flakes, particularly in neat methanol. A similar trend was also observed in isopropanol, trifluoroethanol, and acetonitrile (data not shown).

The SWNT-SBP conjugates were also more active in methanol than enzyme immobilized onto a variety of other flat supports, including highly ordered pyrolytic graphite (HOPG) and self-assembled monolayers (SAMs) of undecanethiolate on gold-coated glass cover slips (FIG. 1a). Finally, SWNT films were prepared by filtering a suspension of SWNTs through a 0.8 µm membrane. SBP adsorbed onto the resulting "SWNT buckypaper" was more active than SBP adsorbed on the flat supports (FIG. 1a), suggesting significantly different behavior under denaturing conditions on these nanoscale supports relative to flat surfaces. Similar results were obtained for multi-walled carbon nanotubes, and gold particles of similar dimensions as the SWNT (data not shown).

In addition to the initial activity, the stability of the SWNT-enzyme conjugates was evaluated in strongly denaturing environments. The half-life of SBP adsorbed onto SWNTs in 100% methanol was at least two-fold longer than that of the enzyme adsorbed onto flat supports (FIG. 1b). The thermostability of the conjugates was also tested at 95° C., a temperature at which native SBP undergoes significant and rapid denaturation. The half-life of SBP adsorbed onto SWNTs at 95° C. was approximately 90 min, ten-fold longer than that of the native enzyme and at least twice that of SBP adsorbed onto other supports (FIG. 1c). A similar enhancement in stability was seen for SBP adsorbed onto SWNT buckypaper (data not shown). These results indicate a dramatic enhancement in stability in harsh environments for SBP adsorbed onto SWNTs. The observed stabilization on SWNTs is not unique to SBP, but is also seen for the unrelated protease subtilisin Carlsberg (SC) (FIG. 1d).

To see if SWNTs render SC more resistant to degradation by autolysis, the storage stability of SWNT-SC and native SC was examined at two different conditions—pH 7.8, at which the protease is most active and pH 4.5, at which the proteolytic activity of SC is negligible. FIG. 3b shows that at both pH conditions, the loss in activity of SC adsorbed on SWNTs is less than that of SC adsorbed on HOPG. The half life of HOPGSC in pH 7.8 was ca. 44 h, about two fold lower than that of SWNT-SC. Interestingly, the activities of adsorbed SC are similar for both the pH conditions, which shows that the loss in activity over time is not due to autolysis, but probably due to protein-surface or protein-protein interactions on the surface of the hydrophobic supports. This further demonstrates the impact of the nanoscale environment on the reported enhanced stability of SWNT-enzyme conjugates.

There are three possible hypotheses that could explain the enhanced stability of enzymes on SWNTs. The first (hypothesis 1) is that protein deactivation in harsh environments is primarily mediated by protein-surface interactions, which are disfavored on highly curved supports such as SWNTs relative to flat supports. An alternative hypothesis (hypothesis 2) stems from the observation that the greater stability of adsorbed enzymes relative to their soluble counterparts is due to greater barriers to unfolding on the supports, as a result of protein-support interactions. Therefore, if proteins have a higher affinity for SWNTs than for other supports, there may be greater barriers to unfolding in harsh environments on SWNTs than on other supports, thereby explaining the higher stability observed on SWNTs. Finally, a third hypothesis is that lateral interactions between adsorbed proteins contribute to protein deactivation in harsh environments, and that these unfavorable "lateral" interactions are suppressed on highly curved supports such as SWNTs relative to those on flat surfaces (FIGS. 2a and b). This third hypothesis is explained in greater detail below.

FIG. 2a depicts proteins adsorbed on a flat support, where x and y represent the distances between adjacent proteins (measured along the protein-substrate interface) along the X and Y axes, respectively. Similarly, $x_f'$ and $y_f'$ represent the center-to-center distance between adjacent proteins along the X and Y-axes, respectively. On a flat support $x=x_f'$, and $y=y_f'$. Furthermore, the surface coverage of proteins is inversely proportional to the product xy. FIG. 2b depicts proteins adsorbed on a cylindrical support, where x and y represent the distances between adjacent proteins (measured along the protein-substrate interface) along the circumference (θ-direction) and the axis of the cylinder, respectively. Here, the values of x and y are identical to those in FIG. 2a. Finally, $x_c'$ and $y_c'$ represent the center-to-center distance between adjacent proteins along the circumference and the axis of the cylinder, respectively. On a cylindrical support, $y_c'=y$; however, $x_c'$ is not equal to x, but is greater than x.

A simple geometric analysis (equation 1) reveals that, $$x_c' = \frac{(R+r)}{R} * x \qquad (1)$$

where R is the radius of the cylinder, and r represents the average dimension of SBP. Consequently, at the same separation along the protein-substrate interface, and the same surface coverage, the curvature of a cylindrical support results in an increase in the center-to-center distance between adjacent proteins (FIG. 2b). If unfavorable interactions between adjacent proteins contribute to their deactivation in harsh environments, then this increase in separation should result in a decrease in the rate of deactivation, and could contribute to the greater protein stability on SWNTs relative to flat supports.

Both experimental data (FIGS. 2c-e) and theoretical analysis (see discussion below and FIGS. 3a-b) are used to distinguish among these hypotheses. The rates of deactivation were measured in aqueous buffer at 95° C. and in methanol for SBP adsorbed onto SWNTs and graphite flakes at different fractional surface coverages. FIGS. 2c and d reveal a strong dependence of the enzymatic deactivation rate on surface coverage, with identical deactivation constants on SWNTs and graphite flakes should persist even at low coverages. Similarly, if the enhanced stability on SWNTs is a result of a greater affinity of the protein for SWNTs (hypothesis 2), the difference in stability should also persist at low surface coverages. The results shown in FIGS. 2c and d are clearly inconsistent with hypotheses 1 and 2, yet they are consistent with hypothesis 3. If unfavorable "lateral" interactions between adsorbed proteins contribute significantly to protein deactivation (hypothesis 3), these interactions, and hence the rate of enzymatic deactivation, should decrease on all supports with decreasing surface coverage (i.e. with an increase in the average separation between adsorbed proteins). Furthermore, hypothesis 3 also predicts that the enhancement in stability on SWNTs relative to graphite flakes should disappear at very low surface coverages.

Additional control experiments were performed to confirm that the similar values of the deactivation constants on SWNT and graphite flakes at low surface coverage are a result of a reduction in unfavorable lateral interactions, and not due to a change in the conformation of the adsorbed protein at low surface coverage. For this purpose, the rates of enzymatic deactivation at 95° C. (FIG. 2e) were measured for the following sets of protein conjugates: 1) SBP adsorbed onto SWNTs and graphite flakes at a high fractional surface coverage (0.75); 2) SBP adsorbed onto SWNTs and graphite flakes at a low fractional surface coverage (0.07); and 3) SBP adsorbed onto SWNTs and graphite flakes at a low fractional surface coverage of 0.07 (same as that for sample set 2), followed by the adsorption of catalytically inactive apo-SBP, yielding a final fractional surface coverage of 0.75 (same as that for sample set 1). While preparing sample set 3, the active protein was allowed to adsorb prior to adsorbing the inactive apo-protein, thereby allowing it to change its conformation on the support (under conditions of low coverage). Furthermore, sample sets 2 and 3, contain the same amount of "active" protein, but differ in the total surface coverage of protein.

As seen in FIG. 2e, the deactivation rate for SWNT-SBP conjugate 3 at 95° C. is identical to that for SWNT-SBP conjugate 1, and is higher than that for SWNT-SBP conjugate 2. Similar trends are seen for the graphite-SBP conjugates. Furthermore, the deactivation rate for the SWNT-SBP conjugate 3 is significantly lower than that for the graphite-SBP conjugate 3. In combination, these results suggest that the decrease in deactivation rate at low surface coverage (FIGS. 2c and d) is not due to a change in the conformation of the adsorbed protein, and provide further support for hypothesis 3.

Finally, a simple model has been developed that allows the quantification of the effect of substrate curvature on the lateral interactions between adsorbed proteins. The model assumes that the proteins are distributed uniformly on the surface. A new variable, S, was introduced to capture the average center-to-center distance between adjacent proteins on the various supports. The term S is defined to be the geometric mean of the center-to-center distances between proteins along the two orthogonal axes; i.e. $S=(x_f'\cdot y_f')^{1/2}$ on a flat support, and $S=(x_c'\cdot y_c')^{1/2}$ on a cylindrical support (FIGS. 2a and b). As discussed above, for the same values of x and y, the value of $x_c'$ is greater than the value of $x_f'$, and therefore the value of S on a cylindrical support is greater than that on a flat support. S may be converted to a dimensionless form ($\epsilon$) by dividing it by the value of S on a flat support at maximum surface coverage ($S_m$); $\epsilon=S/S_m$. FIGS. 2a and b indicate that $S_m$ is equivalent to the geometric mean of the distance between adjacent proteins along the protein-substrate interface along the two orthogonal axes, measured at maximum surface coverage.

The deactivation rates of adsorbed SBP on the various supports, previously plotted as a function of surface coverage (FIGS. 2c and d), are now plotted as a function of the dimensionless variable $\epsilon$ (FIGS. 3a and b). The introduction of $\epsilon$, which now accounts for the curvature of the support, allows the data for the deactivation rates on graphite flakes and SWNTs to collapse onto a single curve, providing further evidence in support of the "lateral-interaction" hypothesis.

The aforementioned model also predicts that the observed enhancement in stabilization should not be unique to SWNTs. Consistent with this prediction, an enhancement in the stability of proteins in harsh environments on other nanostructured supports, including gold nanoparticles, was observed in the experiments described above. This phenomenon results from the radius of curvature of the nanoscale support being commensurate with the dimensions of the protein, as illustrated schematically in FIG. 2b. Consistent with this hypothesis, a scanning electron micrograph of SWNT buckypaper (FIG. 20 shows SWNT bundles having an average diameter of ca. 8 nm. Moreover, the value of SBP's saturation loading on SWNTs (measured to be 655 mg/g) supports this value of the average bundle diameter (16, 23). The average bundle radius is therefore similar to the dimensions of SBP (6.1 nm×3.5 nm×4.0 nm).

These highly stable and active enzyme-nanotube conjugates are ideally suited for designing functional nanocomposites; composites incorporating enzymes, particularly proteases, may be useful for designing anti-fouling or self-cleaning surfaces. Previous applications have been limited by enzyme leaching from the matrix, low enzyme loading, and low activity of the incorporated enzymes because of poor stability in the harsh abiotic environment. The stable SWNT-enzyme composites should form highly stable biocatalytic films. To that end, SWNT-SC conjugates were dispersed in poly(methyl methacrylate) (pMMA) (FIG. 4a) and the enzymatic activities of the films were measured. The pMMA-SWNT-SC films retained >90% of their initial activity over 30 days in aqueous buffer. Furthermore, the high surface area per unit weight of the SWNTs resulted in high enzyme loadings in the films, and consequently, the films were over 30 times more active than those containing identical amounts of graphite-SC conjugates (FIG. 4b). The control pMMA-SC films exhibited significant leaching, resulting in a nearly complete loss of activity after washing (FIG. 4b).

The proteolytic activity of the biocatalytic films will allow the preparation of antifouling and antimicrobial surfaces, for example those that may be used on surgical instruments, implants, diagnostics, bioreactors, and other surfaces prone to contamination. The attachment of bacteria to surfaces, which can result in the buildup of biofilms, is often mediated by protein adsorption that will most likely be prevented by making surfaces protein-resistant. Biocatalytic nanocomposites that resist non-specific protein adsorption were designed (FIG. 4c). To assess the protein resistance of these materials, the biocatalytic films were exposed to concentrated solutions (1 mg/mL) of the plasma protein human serum albumin (HSA) continuously for 6 days. pMMA-SWNT-SC films were able to reduce the nonspecific binding of HSA by ca. 75% when compared to films without SC (FIG. 4c). SDS-PAGE of HSA incubated with pMMA-SWNT-SC films revealed proteolytic breakdown products (data not shown), suggesting that this decrease in HSA binding is due to the proteolytic degradation of the bound HSA and the subsequent desorption of the peptide fragments rendering the film self-cleaning Biocatalytic films that also incorporated a second protease, trypsin (TRY), adsorbed onto SWNTs to provide a broader range of proteolytic cleavage sites on the HSA, yielded further reduction in the extent of nonspecific protein adsorption, with as much as ca. 95% lower binding when compared with the enzyme-free film (FIG. 4c). The biocatalytic films demonstrate the high stability required for continuous operation in commercial environments. When challenged with a fresh sample of HSA (1 mg/mL) every 3 days, the pMMA-SWNT-enzyme conjugates led to ~50 fold decrease in HSA binding over 30 days. These films are also active in high salt buffers and at elevated temperatures.

A thermal analysis was used to examine the pMMA films to ensure that the changes in the physical properties of the polymer are minimal due to the incorporation of the SWNT-enzyme conjugates. The films were prepared as before and the glass-transition temperature (Tg) of the films were measured. The Tg values of pMMA and pMMA-SWNT-SC films were similar; x and y respectively.

In addition to polymeric composites, films composed solely of SWNTs and enzymes were prepared by filtering suspensions of SWNT-SC and SWNT-TRY conjugates through a 0.8 µm membrane (FIG. 4a). These "biocatalytic buckypapers" have enzyme loadings as high as 30% (w/w), which are among the highest loadings reported to date. As shown in FIG. 4c, these films showed negligible protein adsorption after 6 days (>99% reduction in the amount of protein adsorption compared to the enzyme-free film).

The enhanced stability of proteins adsorbed on nanotubes, in addition to the other attractive features (minimal leaching, high surface area per unit weight, and high strength to name a few) will thus be used in applications ranging from biosensing to biomedical devices, which would require highly stable protein-nanotube conjugates. The experimental results and the accompanying theoretical analysis shown here indicate that the observed enhancements in protein stability are not unique to nanotubes and will also be obtained with other nanomaterials. The ability to enhance protein function by interfacing them with nanomaterials will have profound impact on the design of biosensors, biorecognition probes, protein chips, biofuel cells, vaccines, novel composites and supports for biotransformations, drug delivery systems, and self-cleaning materials.

Figure Legends

Figure 1:
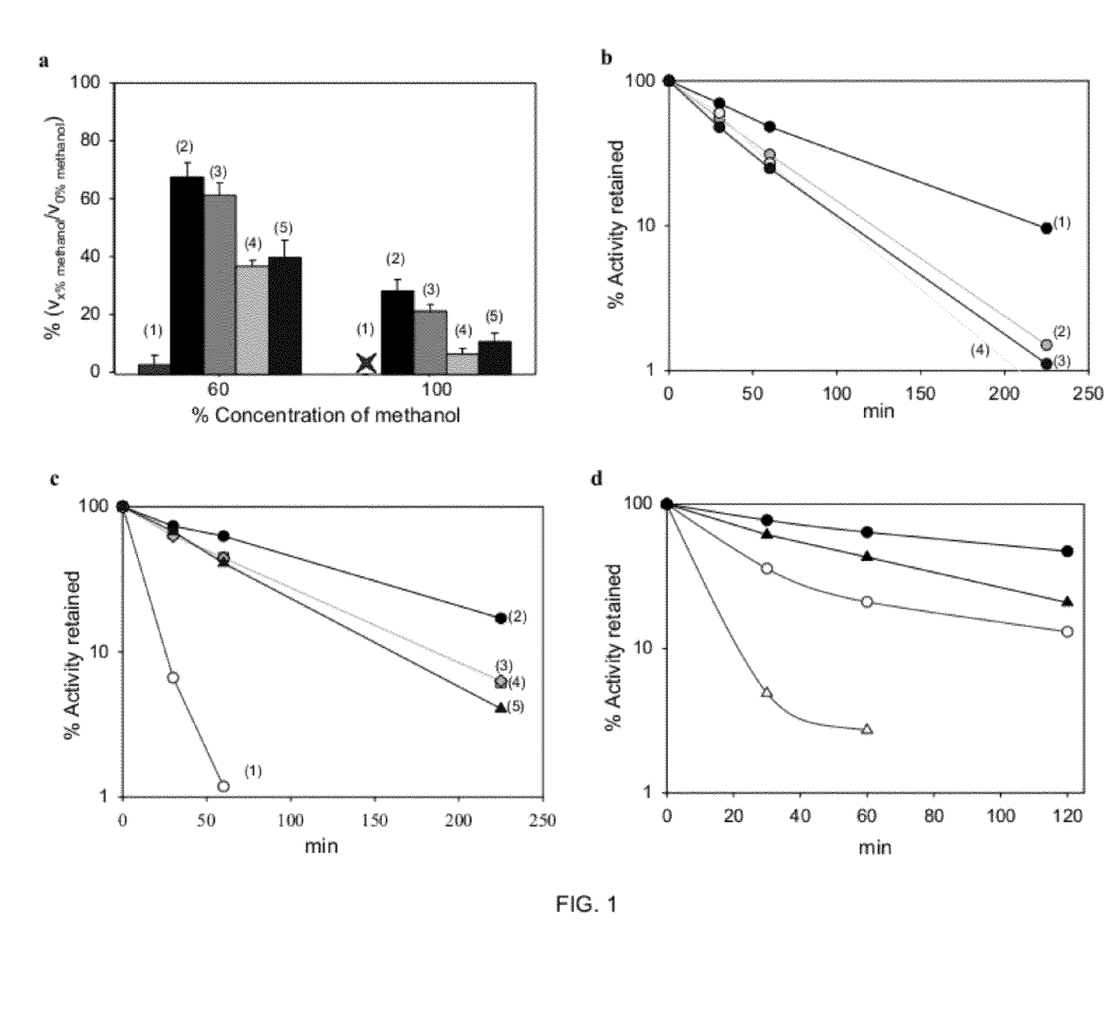
FIG. 1(a) is a bar graph showing the percent activity of soybean peroxidase in its native state and on various supports in various concentrations of methanol.
FIG. 1(b) is a line graph showing the time-dependent deactivation of soybean peroxidase on various supports in 100% methanol.
FIG. 1(c) is a line graph showing the time-dependent deactivation of soybean peroxidase in its native state and on various supports in 95° C. aqueous solutions.
FIG. 1(d) is a line graph showing the time-dependent deactivation of subtilisin Carlsberg in its native state and on various supports at various temperatures.

FIG. 1 Retention of enzymatic activity when exposed to harsh environments. (a) The initial activity (v) in solutions containing methanol relative to the activity in aqueous buffer for native SBP (1) and SBP adsorbed on various supports—SWNTs (2), buckypaper made out of SWNTs (3), HOPG (4), and graphite flakes (5). The asterisk indicates no activity of the native SBP in 100% (<0.01% $H_2O$) methanol. (b) Time-dependent deactivation of SBP in 100% methanol on various supports—SWNTs (1), HOPG (2), SAM of undecanethiolate on gold (3), and graphite flakes (4). For (b)-(d), the activities are normalized relative to the initial activity (activity at t=0 min), and each data point represents an average of triplicate measurements with standard error <10%. (c) Time-dependent deactivation of SBP at 95° C. on various supports—native SBP (1 open circles), SWNTs (2 black circles), HOPG (3 diamonds), SAM of undecanethiolate on gold (4 open squares), and graphite flakes (5 triangles). (d) Time-dependent deactivation of SC on various supports in aqueous buffer—native SC (open circles), SC adsorbed on SWNTs (black circles) at 50° C. (open circles) and 70° C. (open triangles).

Figure 2:
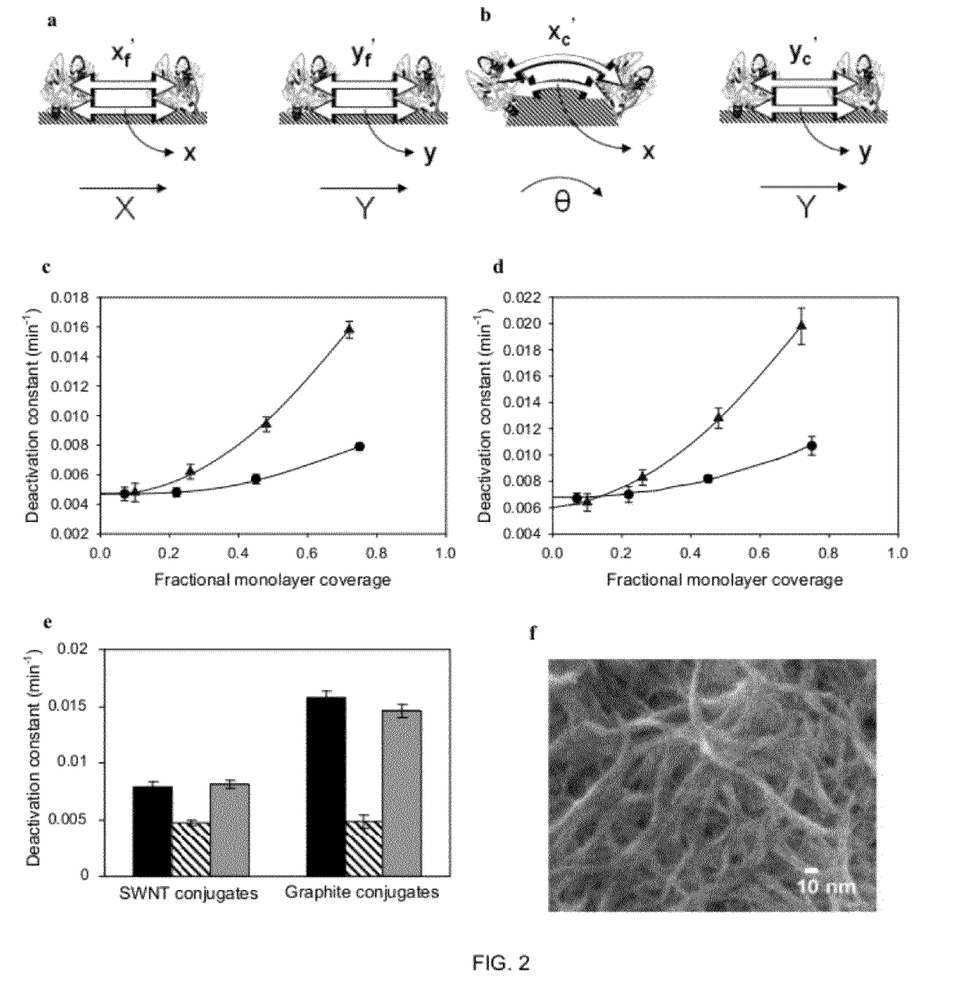
FIG. 2(a) is a schematic showing soybean peroxidase on a flat support.
FIG. 2(b) is a schematic showing soybean peroxidase on a curved support.
FIG. 2(c) is a line graph showing deactivation constants from soybean peroxidase on various supports as a function of surface area coverage in 95° C. aqueous solutions.
FIG. 2(d) is a line graph showing deactivation constants for soybean peroxidase on various supports as a function of surface area coverage in 100% methanol.
FIG. 2(e) is a bar graph showing deactivation constants for soybean peroxidase on various supports at different amounts of surface area coverage.
FIG. 2(f) is a micrograph of signal walled nanotubes on buckypaper.

FIG. 2 Effect of lateral interactions on the deactivation constants of SBP adsorbed onto different supports. (a) Schematic depicting SBP molecules adsorbed onto a "flat" support. (b) Schematic (drawn approximately to scale) depicting SBP molecules adsorbed onto a cylindrical support. The curvature of the support increases the center-to-center distance between adjacent proteins ($x_c'$), relative to the distance on a "flat" support ($x_f'$). (c) Deactivation constants for SBP adsorbed onto SWNTs (circles) and graphite flakes (triangles) as a function of surface coverage at 95° C. In (c) and (d), error bars indicate the standard deviation of triplicate measurements. (d) Deactivation constants for SBP adsorbed onto SWNTs (circles) and graphite flakes (triangles) as a function of surface coverage in 100% methanol. (e) Deactivation constants for SBP adsorbed onto SWNTs and graphite flakes at a fractional surface coverage of 0.75 (black bars), a fractional surface coverage of 0.07 (hatched bars), and a fractional surface coverage of 0.07 for SBP, with a "total" surface coverage of 0.75 for SBP and apo-SBP (gray bars). (f) SEM image of a typical SWNT buckypaper.

Figure 3:
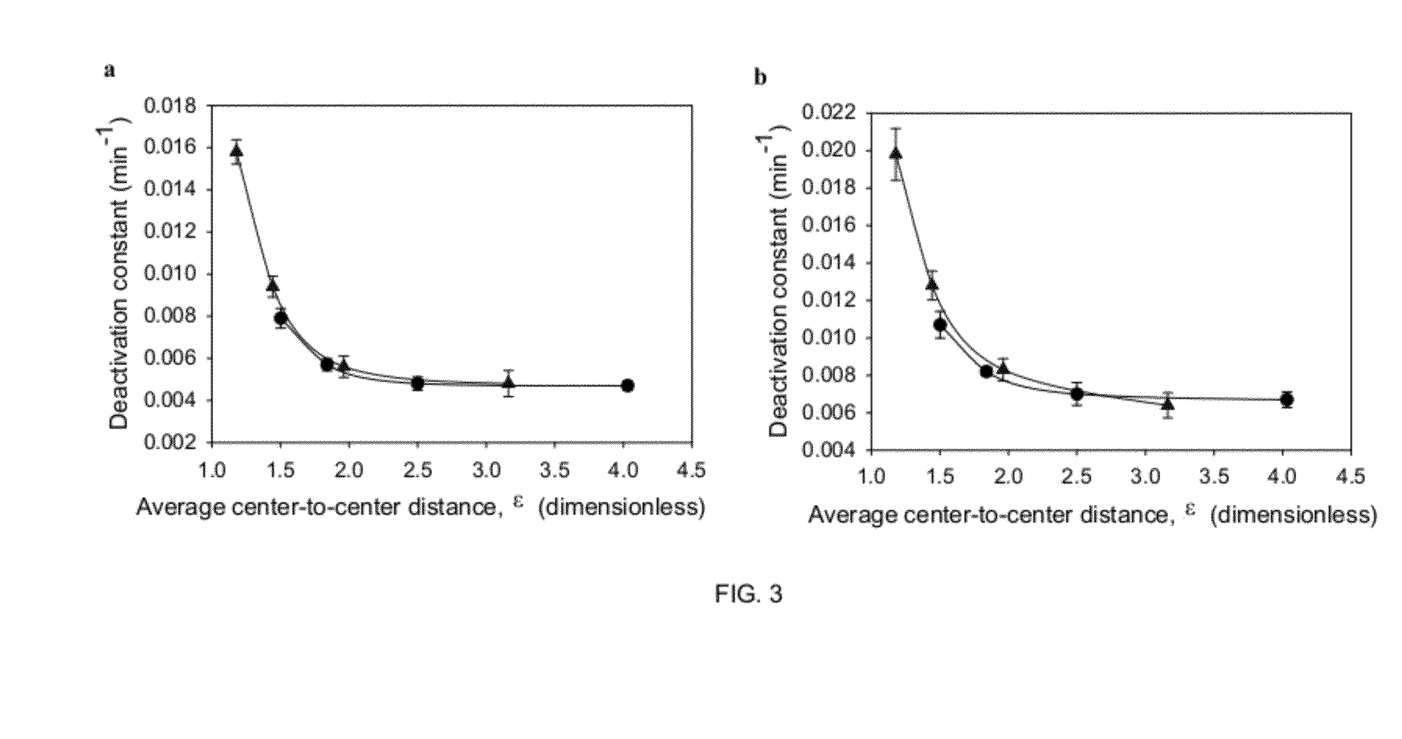
FIG. 3(a) is a line graph showing deactivation constants for soybean peroxidase on various supports in 95° C. aqueous solutions.
FIG. 3(b) is a line graph showing deactivation constants for soybean peroxidase on various supports in 100% methanol.

FIG. 3 Influence of the center-to-center distance between adsorbed proteins on the deactivation rate. Deactivation constants for SBP adsorbed onto SWNTs (circles) and graphite flakes (triangles) as a function of the dimensionless variable $\epsilon$ (a) at 95° C. and (b) in 100% methanol. Error bars indicate the standard deviation of triplicate measurements. The introduction of the dimensionless variable 8 enables the deactivation rates on different supports to be collapsed onto a single curve.

Figure 4:
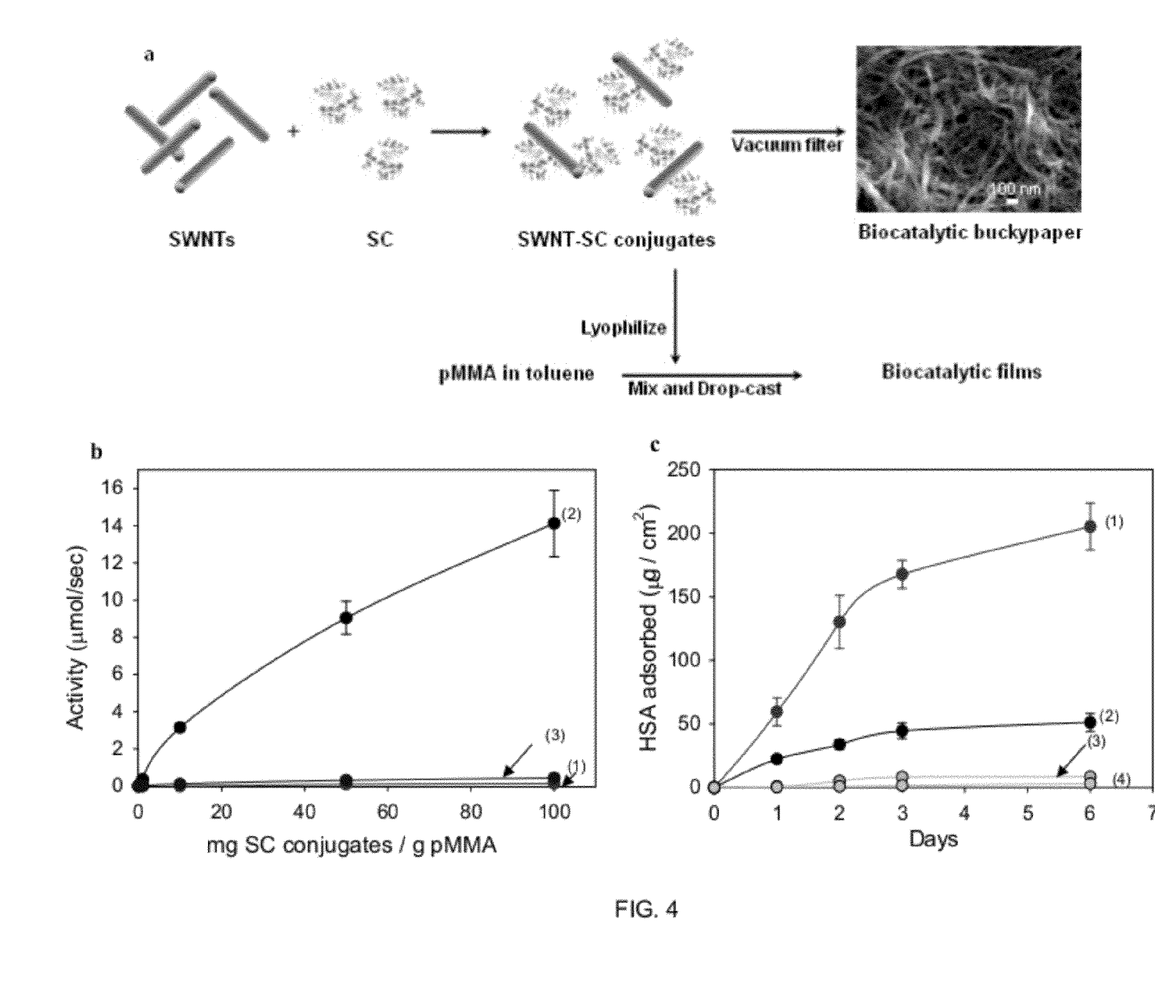
FIG. 4(a) is a schematic showing the preparation of biocatalytic films.
FIG. 4(b) is a line graph showing the concentration-dependent activity of subtilisin Carlsberg on various supports on pMMA films.
FIG. 4(c) is a line graph showing the amount of human serum albumin adsorbed to pMMA films without and with subtilisin Carlsberg on single-walled nanotubes attached to the films.

FIG. 4 Enzymatic activities of biocatalytic films. (a) Preparation of biocatalytic films along with a SEM image of a typical biocatalytic buckypaper. (b) Activities of native SC (1), SC adsorbed on SWNTs (2), and SC adsorbed on graphite powder (3) in pMMA films as a function of the amount of SC conjugates loaded into the films. The activities were measured after the films were washed extensively with aqueous buffer. (c) Protein-resistant properties of the biocatalytic films—amount of HSA adsorbed onto plain pMMA films (control, 1), pMMA-SWNT-SC films (2), pMMA-SWNT-SC-TRY films (3) and SWNT-SC-TRY buckypaper (4). Error bars indicate the standard deviation of triplicate measurements.

While this invention has been particularly shown and described with references to preferred embodiments thereof, it will be understood by those skilled in the art that various changes in form and details may be made therein without departing from the scope of the invention encompassed by the appended claims.

What is claimed:

1. A composition comprising:
   (a) nanoparticles; and
   (b) proteins, wherein said proteins are bound to external surfaces of said nanoparticles and wherein each of said external surfaces has a radius of curvature that is within 1 order of magnitude of the dimensions of each of said proteins bound to said nanoparticles, wherein the stability of the bound proteins is greater than the stability of the proteins bound to surfaces of the same material as that of said nanoparticles but which forms a flat surface; and wherein said proteins are enzymes.

2. The composition of claim 1, wherein the composition is in a liquid medium, and wherein said liquid medium is selected from the group consisting of an aqueous medium at a temperature greater than about 40° C., less than about 10° C., an aqueous medium whose pH is less than about pH 6.5, an aqueous medium whose pH is greater than about pH 7.5, an aqueous medium with a salinity of at least about 0.3M NaCl, and a non-aqueous medium.

3. The composition of claim 1, wherein said nanoparticles are selected from the group consisting of single-walled carbon nanotubes, multi-walled carbon nanotubes, gold or other metallic nanoparticles, semi-conducting nanoparticles, metal oxide nanoparticles, quantum dots, functionalized silica nanoparticles, and mixtures thereof.

4. The composition of claim 1, wherein said proteins are bound to said nanoparticles through hydrophobic bonding, hydrophilic bonding, ionic bonding, covalent bonding, or non-covalent bonding.

5. An article of manufacture comprising the composition of claim 1 bound to a macroscopic surface.

6. The article of manufacture of claim 5, wherein said macroscopic surface is selected from the group consisting of a polymer, a polymeric film, a metal, a metal alloy, and combinations thereof.

7. The article of manufacture of claim 5, wherein said article is incorporated in a member of the group consisting of a biosensor, a biochip, a biofuel cell, a drug delivery system, an antimicrobial film, a paint antifouling film, and a lubricant antifouling film.

8. A method of making a device containing a composition which can enzymatically act on one or more substances in a solution comprising:
   attaching the composition of claim 1 to a working surface of said device where said working surface will be in contact with said solution when the enzyme activity of said enzymes is desired;
   thereby forming the device.

9. The method of claim 8, wherein the solvent of said solution is selected from the group consisting of an aqueous medium at a temperature greater than about 40° C., less than about 10° C., an aqueous medium whose pH is less than about pH 6.5, an aqueous medium whose pH is greater than about pH 7.5, a liquid hydrocarbon medium, and an aqueous medium with a salinity of at least about 0.3 M NaCl.

10. The method of claim 8, wherein said nanoparticles are selected from the group consisting of single-walled carbon nanotubes, multi-walled carbon nanotubes, gold or other metallic nanoparticles, semi-conducting nanoparticles, metal oxide nanoparticles, quantum dots, functionalized silica nanoparticles, and mixtures thereof.

11. The method of claim 8, wherein said enzymes are bound to said nanoparticles through hydrophobic bonding, hydrophilic bonding, ionic bonding, covalent bonding, and non-covalent bonding.

12. A method of detecting an analyte in a solution comprising:
   (a) contacting said solution containing said analyte with the composition of claim 1;
   (b) allowing said enzymes to enzymatically act on said analyte, thereby forming a product that is detectable by external means; and
   (c) detecting said product by said external means, thereby detecting said analyte.

13. The method of claim 12, wherein said liquid medium is selected from the group consisting of an aqueous medium at a temperature greater than about 40° C., less than about 10° C., an aqueous medium whose pH is less than about pH 6.5, an aqueous medium whose pH is greater than about pH 7.5, a liquid hydrocarbon medium, and an aqueous medium with a salinity of at least about 0.3 M NaCl.

14. The method of claim 12, wherein said nanoparticles are selected from the group consisting of single-walled carbon nanotubes, multi-walled carbon nanotubes, gold or other metallic nanoparticles, semi-conducting nanoparticles, metal oxide nanoparticles, quantum dots, functionalized silica nanoparticles, and mixtures thereof.

15. The method of claim 12, wherein said enzymes are bound to said nanoparticles through hydrophobic bonding, hydrophilic bonding, ionic bonding, covalent bonding, or non-covalent bonding.

16. A method of reducing the fouling of a surface by a substance present in a solution comprising:
   (a) contacting said solution containing said substance with said surface wherein a composition of claim 1 is attached to said surface; and
   (b) allowing said enzymes to enzymatically degrade said substance, thereby reducing the amount of said substance in said solution and the fouling adherence of said substance to said surface.

17. The method of claim 16, wherein said liquid medium is selected from the group consisting of an aqueous medium at a temperature greater than about 40° C., less than about 10° C., an aqueous medium whose pH is less than about pH 6.5, an aqueous medium whose pH is greater than about pH 7.5, a liquid hydrocarbon medium, and an aqueous medium with a salinity of at least about 0.3 M NaCl.

18. The method of claim 16, wherein said nanoparticles are selected from the group consisting of single-walled carbon nanotubes, multi-walled carbon nanotubes, gold or other metallic nanoparticles, semi-conducting nanoparticles, metal oxide nanoparticles, quantum dots, functionalized silica nanoparticles, and mixtures thereof.

19. The method of claim 16, wherein said enzymes are bound to said nanoparticles through hydrophobic bonding, hydrophilic bonding, ionic bonding, covalent bonding, or non-covalent bonding.

* * * * *